(12) United States Patent
Shang et al.

(10) Patent No.: US 10,369,165 B2
(45) Date of Patent: Aug. 6, 2019

(54) **COMPOSITION CONTAINING ACTIVE COMPONENTS OF *DRACOCEPHALUM MOLDAVICA* L. AGAINST MYOCARDIAL ISCHEMIA-REPERFUSION INJURY**

(71) Applicant: Nanjing Ruiying Runze Biopharmaceutical Technology Co., Inc., Nanjing, Jiangsu (CN)

(72) Inventors: Jing Shang, Jiangsu (CN); Dongsheng Yu, Jiangsu (CN); Youqing Tian, Jiangsu (CN); Huali Wu, Jiangsu (CN); Lin Ding, Jiangsu (CN); Jun Liu, Jiangsu (CN)

(73) Assignee: NANJING RUIYING RUNZE BIOPHARMACEUTICAL TECHNOLOGY CO., INC., Nanjing, Jiangsu (CN)

( * ) Notice: Subject to any disclaimer, the term of this patent is extended or adjusted under 35 U.S.C. 154(b) by 0 days.

(21) Appl. No.: 15/531,763

(22) PCT Filed: Mar. 6, 2015

(86) PCT No.: PCT/CN2015/073822
§ 371 (c)(1),
(2) Date: May 31, 2017

(87) PCT Pub. No.: WO2016/086543
PCT Pub. Date: Jun. 9, 2016

(65) Prior Publication Data
US 2017/0266216 A1 Sep. 21, 2017

(30) Foreign Application Priority Data

Dec. 3, 2014 (CN) .......................... 2014 1 0724953

(51) Int. Cl.
*A61K 36/53* (2006.01)
*A61K 31/352* (2006.01)
*A61K 31/7048* (2006.01)

(52) U.S. Cl.
CPC ........ *A61K 31/7048* (2013.01); *A61K 31/352* (2013.01); *A61K 36/53* (2013.01)

(58) Field of Classification Search
None
See application file for complete search history.

(56) References Cited

FOREIGN PATENT DOCUMENTS

CN  102697769 A  10/2012

OTHER PUBLICATIONS

Süzgeç, S., Meriçli, A. H., Houghton, P. J., & Çubukçu, B. (2005). Flavonoids of Helichrysum compactum and their antioxidant and antibacterial activity. Fitoterapia, 76(2), 269-272. (Year: 2005).*
Sun, X., Sun, G. B., Wang, M., Xiao, J., & Sun, X. B. (2011). Protective effects of cynaroside against H2O2-induced apoptosis in H9C2 cardiomyoblasts. Journal of cellular biochemistry, 112(8), 2019-2029. (Year: 2011).*
Tatli, A. (2004). Chemical constituents of *Verbascum* L. species. FABAD J Pharm Scieces, 29, 93-107. (Year: 2004).*
Li, W., Shi, L. L., Han, L. Q., & Zhang, J. (2013). Development and validation of a RP-HPLC method for simultaneous determination of salicin and eight flavonoids in leaves of Salix Matsudana Koidz. Acta Chromatographica, 25(4), 735-743. (Year: 2013).*
Definition of "compound" and "composition" in Grant and Hackh's chemical dictionary, 5th Ed. McGraw Hill. 1987.p. 148. ISBN 0-07-024067-1 (Year: 1987).*
Liao Peihu et al.; "Cardioprotective Effects of Luteolin During Ischemia-Reperfusion Injury in 1-5 Rats"; Circulation Journal, vol. 75; Dated Feb. 28, 2011; pp. 443-449.
International Search Report and Written Opinion from Corresponding Application No. PCT/CN2015/073822; dated Aug. 14, 2015.
Kim Dosung, et al. "Kaempferol Protects Ischemia/Reperfusion-Induced Cardiac Damage Through the Regulation of Endoplasmic Reticulum Stress"; Immunopharmacology and Immunotoxicology; vol. 30; Dec. 31, 2008; pp. 257-270.

* cited by examiner

*Primary Examiner* — Shaojia A Jiang
*Assistant Examiner* — Dale R Miller
(74) *Attorney, Agent, or Firm* — Pearne & Gordon LLP

(57) ABSTRACT

Disclosed is a composition containing active components of *Dracocephalum moldavica* L. against myocardial ischemia-reperfusion injury (MIRI). The composition consists of active components and a pharmaceutically acceptable carrier, wherein the active components comprise luteolin, kaempferol and luteolin-7-O-glucoside. Pharmacodynamic experiments show that these three components can be combined together to synergistically treat myocardial ischemia-reperfusion injury.

4 Claims, 2 Drawing Sheets

COMPOSITION CONTAINING ACTIVE COMPONENTS OF *DRACOCEPHALUM MOLDAVICA* L. AGAINST MYOCARDIAL ISCHEMIA-REPERFUSION INJURY

BACKGROUND OF THE INVENTION

1. Field of the Invention

The present invention relates to the natural medicine field, and particularly, to the compatible composition comprising the active components of luteolin, kaempferol and luteolin-7-O-glucoside of *Dracocephalum moldavica* L.

2. Description of the Related Art

Cardiovascular disease is one of the leading causes of death worldwide, with the highest mortality and disability rate of all kinds of diseases. Myocardial ischemia-reperfusion injury (MIRI) is a severe toxic reaction including arrhythmia, myocardial contraction dysfunction, irreversible myocardial reperfusion injury, etc. MIRI happens when blood supply returns to the tissue after a period of myocardial ischemia, and it seriously affects the treatment of disease. In recent years, ischemia-reperfusion injury attracts more and more attention because of the wide application of the clinical treatments such as coronary artery bypass grafting. Therefore, development of drugs for prevention and treatment of MIRI is a crucial problem to be urgently solved in clinic.

There are many hypotheses for the mechanism of reperfusion injury, mainly include excessive production of oxygen free radical, overload of $Ca^{2+}$, inflammation activated by endothelial cells and neutrophils, irreversible myocardial injury which is primarily apoptosis, and so on. The drugs that commonly used for treating MIRI mainly aim at single risk factor, for example, glutathione and vitamin E, which are free radical scavenger and anti-oxidant; drugs for relieving calcium overload, such as Nifedipine which is $Ca^{2+}$ channel blocker, calcitonin gene-related Peptide CGRP, adenosine, etc.; drugs for protecting vascular endothelium, such as angiotensin converting enzyme inhibitors (ACEI), endothelium-derived NO, etc.; drugs for inhibiting the release of inflammatory mediators, such as Ulinastatin; and the application of Chinese traditional drugs, including ginsenoside, *Pueraria*, etc. However, it still needs further investigation to develop safer and more effective drugs for the treatment of MIRI.

Traditional Chinese medicine has formed distinctive theoretical system through thousands years of history, and provides a precious resources for modern research and development of Chinese medicine. However, because compound composition of the traditional Chinese medicine is complex, and quality control is difficult, thereby application of Chinese medicine against MIRI in broader range is limited. Component Chinese medicine can be made by removing invalid and toxic components from complex Chinese medicine, extracting the active components for the disease, and optimizing the ratio thereof to exert their medical effect at the highest level.

Chinese medicine *Dracocephalum moldavica* is *Dracocephalum moldavica* L., which belongs to genus *Dracocephalum* in Labiatae family, and the whole grass aboveground is officinal, with the effect of clearing lungs, relieving exterior syndromes, cooling livers and homeostasis. The known components separated from *Dracocephalum* includes: flavonoids, triterpenes, steroids, phenylpropanoids, iridoids, essential oil and so on. The results of previous studies show that the effects of luteilon, kaempferol and luteolin-7-O-glucoside in MIRI protection are different: luteilon can increase mitochondrial membrane potential, improve the function of myocardial contraction; kaempferol can reduce mitochondrial $Ca^{2+}$, inhibit the activity of SHP-2, PTEN and maintain the heart rate; luteolin-7-O-glucoside can reduce the level of cytoplasmic $Ca^{2+}$ and prevent the oxygen free radical damage. The structural formulae are as follows:

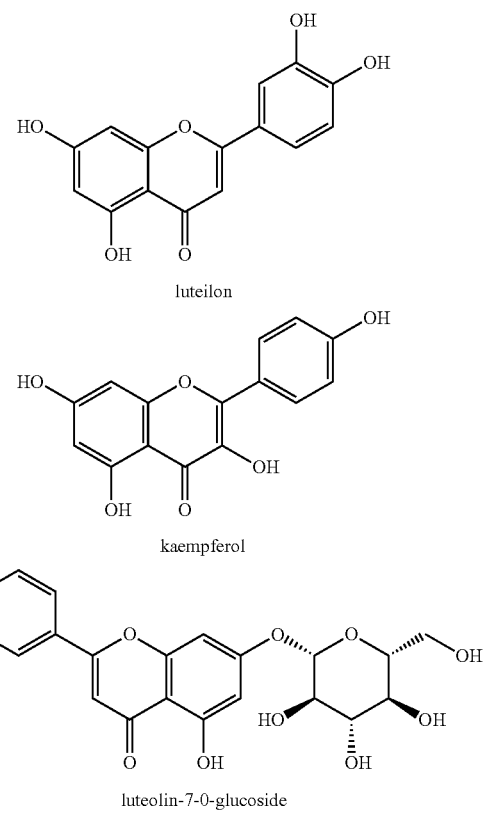

So far, it has not yet been reported to formulate a drug by using luteilon, kaempferol and luteolin-7-O-glucoside to treat MIRI.

SUMMARY OF THE INVENTION

The present invention discloses a compound pharmaceutical composition, having pharmaceutical active components comprising luteilon, kaempferol and luteolin-7-O-glucoside. It is proved by pharmacodynamic tests that the three components, which are combined together, can treat MIRI synergistically.

Test results show that compatible composition of luteilon, kaempferol and luteolin-7-O-glucoside, with a molar concentration ratio of 0.4-2.8:1.5-4.7:0.2-3.1, can obviously decrease the injury and apoptosis rate of rat primary cardiac myocytes induced by hypoxia/reoxygenation, and its myocardial protecting effect can reach 70% or more on average. Preferably, the molar ratio of the three components is 0.7-2.2:2.1-4.1:0.6-2.4, and in this range, the myocardial protecting effect of the composition can reach 80% or more on average. More preferably, the molar ratio of the three components is 1.1-1.6:2.8-3.5:1.0-1.7, and in this range, the myocardial protecting effect of the composition can reach 90% or more on average.

The compound pharmaceutical composition of the present invention can be made into various preparations in pharmaceutical field, such as tablet, granule, injection, dripping pill, capsule, aerosol, turunda, plaster and so on, and can be administered by oral route, or by intravenous, muscle, subcutaneous injection or other kinds of injection, or by intraoral, per rectum, per vaginam, per cutem absorption, or by intranasal inhalation, or administered in any pharmaceutical formulation containing the active components, and in any pharmaceutically acceptable formulation. In the composition of the present invention, in addition to the pharmaceutical active components, one or more pharmaceutically commonly used pharmaceutical preparation necessities can be added as pharmaceutically acceptable carrier, such as excipients, diluent, binder, stabilizers and so on, in addition, some chemical additives can be added, such as pigment, preservative, flavoring agent and so on.

In the following, pharmacodynamic tests and results are described.

The method of preparing the compatible composition solution of the tested drug is as follows: dimethyl sulfoxide is used as the solvent and luteilon, kaempferol and luteolin-7-O-glucoside are dissolved, wherein the final concentration of dimethyl sulfoxide is less than 0.1%. The ratios of three components in different groups of composition are shown in table 1.

TABLE 1

Constitution of compatible compositions (molar concentration ratio)

| group number | luteilon | kaempferol | luteolin-7-0-glucoside |
|---|---|---|---|
| 1 | 1.000 | 2.509 | 2.491 |
| 2 | 1.516 | 1.508 | 2.976 |
| 3 | 1.000 | 4.000 | 1.000 |
| 4 | 1.299 | 3.096 | 1.605 |
| 5 | 1.946 | 2.096 | 1.958 |
| 6 | 2.187 | 2.813 | 1.000 |
| 7 | 1.001 | 1.000 | 3.999 |
| 8 | 2.515 | 1.000 | 2.485 |
| 9 | 2.889 | 1.721 | 1.390 |
| 10 | 4.000 | 1.000 | 1.000 |
| 11 | 3.161 | 1.000 | 1.839 |
| 12 | 6.000 | 0.000 | 0.000 |
| 13 | 0.000 | 6.000 | 0.000 |
| 14 | 0.000 | 0.000 | 6.090 |

Note:
each compatible composition is consisted of luteilon, kaempferol and luteolin-7-O-glucoside, and their total molar concentration is 30 μM. Table 1 shows the molar concentration ratio of the active components.

I. Influence of the Drug on the Activity of the Rat Primary Cardiac Myocytes.

Rat cardiac myocytes H9c2 in logarithmic growth phase are taken. After digestion, the cells are resuspended with DMEM medium (containing 10% FBS), then inoculated into 96-well plate and normally cultured in incubator of 37° C. and 5% $CO_2$. After entering logarithmic growth phase, the cells are divided into following groups for experiment: (1) normal culture group (Control group): during the experiment, cells are normally cultured in incubator of 37° C. and 5% $CO_2$; (2) $N_2H/R$ Model group (Model group): normal culture fluid for the experimental cells in logarithmic growth phase is replaced with glucose-free Earle's solution which has been previously saturated with mixture of 95% $N_2$+5% $CO_2$ for 1 hour. Then the cells are cultured in hypoxic condition for 6 h at 37° C. in constant-temperature incubator introduced with the mixture of 95% $N_2$+5% $CO_2$. Then the hypoxia treated cells are subjected to reoxygenation in normal condition for 5 h with the high glucose medium DMEM (containing 10% FBS) which has been previously saturated with mixture of 95% air+5% $CO_2$. (3) pre-treated compatible group of luteilon, kaempferol and luteolin-7-O-glucoside: H9c2 cells are preincubated for 12 h with luteilon, kaempferol and luteolin-7-O-glucoside combined in different ratios. Then, the normal culture solution is replaced with glucose-free Earle's solution which has been previously saturated with mixture of 95% $N_2$+5% $CO_2$ for 1 hour. After anoxic treatment for 6 h with $N_2$ anoxic tank, the cells are subjected to reoxygenation for 5 h in normal culture condition with normal culture solution; meanwhile the cells are incubated with the administration of each compatible drug. After treatment, 20 μg/ml MTT is added, and each experimental group is cultured for 4 h, then MTT is solved in 150 μl DMSO. OD of each well is read by ELISA meter at wavelength of 490 nm, and activity of cells is determined. The results are shown in table 2.

TABLE 2

Influence of different compatible compositions on apoptosis of rat H9c2 cardiac myocytes after hypoxia/reoxygenation injury

| group number | administration (μM) dose | protection rate of (%) cell activity |
|---|---|---|
| 1 | 30 | 99.46 ± 4.19 |
| 2 | 30 | 93.49 ± 3.69 |
| 3 | 30 | 90.19 ± 6.79 |
| 4 | 30 | 99.98 ± 0.78 |
| 5 | 30 | 96.88 ± 5.14 |
| 6 | 30 | 91.17 ± 9.79 |
| 7 | 30 | 95.85 ± 3.47 |
| 8 | 30 | 92.59 ± 6.26 |
| 9 | 30 | 96.04 ± 3.25 |
| 10 | 30 | 85.32 ± 5.68 |
| 11 | 30 | 81.39 ± 11.91 |
| 12 | 30 | 81.93 ± 7.18 |
| 13 | 30 | 76.97 ± 6.67 |
| 14 | 30 | 78.57 ± 4.54 |

Groups 1 to 11 in table 2 are formed by combining luteilon, kaempferol and luteolin-7-O-glucoside; the compatible groups 12 to 14 are individual luteilon, kaempferol and luteolin-7-O-glucoside, respectively. Compared with the individual compound groups 12 to 14, the effect of the compatible groups to protect cells is better. At the same time, each compatible group is different significantly in protecting cardiac myocytes of hypoxia/reoxygenation injury, and the protection effects of compatible groups 1, 4, 5, 7 and 9 are notable.

II Analysis of Compatible Synergistic Effect of the Three Individual Compounds

TABLE 3

Analysis of compatible synergistic effect of the active ingredient of *Dracocephalum moldavica* L.

| interaction term | estimated coefficient | freedom | standard error | 95% confidence lower limit | 95% confidence upper limit |
|---|---|---|---|---|---|
| A-A | 0.80 | 1 | 0.063 | 0.65 | 2.44 |
| B-B | 0.71 | 1 | 0.063 | 0.63 | 2.36 |
| C-C | 0.79 | 1 | 0.063 | 0.65 | 2.32 |
| AB | 0.68 | 1 | 0.43 | −0.33 | 5.40 |
| AC | 3.366E−003 | 1 | 0.39 | −0.90 | 4.83 |
| BC | 1.16 | 1 | 0.41 | 0.20 | 4.95 |
| ABC | 6.48 | 1 | 1.52 | 4.96 | 8.00 |

In the Table, A represents luteilon, B represents kaempferol, and C represents luteolin-7-O-glucoside. Analyzing the interaction estimated coefficients in Table 3, larger coefficients indicate stronger interaction among the compounds. It can be seen, regarding protecting the cell activity from hypoxia/reoxygenation injury, the interaction among the three compounds luteilon, kaempferol and luteolin-7-O-glucoside is the strongest, which is stronger than the interaction between every two drugs of the three, and stronger than the effect of each individual compound.

III. 3D Plot and Contour Map Used for Calculating Compatible Ratio by Response Surface Analysis Method Using D-Optimal experimental design method in the mixture experimental design, calculation is carried out by using response surface analysis method and using Design expert 8.05b software. Choosing D-optimal in the Mixture option, analysis is carried out by entering compatible ratio of the compatible groups and the test results in Table 2. The test results are fitted by choosing the model which has the maximum value in the adjusted R-square and predictive R-square in the results, and the model obtained by fitting is used to predict the effect of various ratios of luteilon, kaempferol and luteolin-7-O-glucoside on decreasing the lipid droplet content, thus 3D-response surface plot and corresponding contour map could be obtained. See FIG. 1.

Dots in the 3D plot in FIG. 1 represent test true values, and the curved surface is formed from the predictive values of luteilon, kaempferol and luteolin-7-O-glucoside in various ratios. The response results in FIG. 1 is analyzed, F value is 4.56, and the multiple correlation coefficient $R^2$ is 0.7673, indicating that the model fits the true situation well. The signal to noise ratio (Adeq Precision) is 5.727, indicating the high reliability, so this method can be used to predict response values.

It can be obtained from the analysis results of 3D plot that, when the molar concentration ratio among luteilon, kaempferol and luteolin-7-O-glucoside is (1.1-1.6):(2.8-3.5):(1.0-1.7), the protection rate of cell activity can reach 90% or more, and when the molar concentration ratio is (0.7-2.2):(2.1-4.1):(0.6-2.4), the protection rate of cell activity can reach 80% or more.

Subsequently, three compatible ratios of 1, 3, 11 are selected in the 3D plot, representing the protective effects of cell activity from good to bad, respectively, and the compatible ratios of these three points are confirmed with primary cardiac myocytes.

IV Influence of the Compatible Composition on the Activity of Rat Primary Cardiac Myocytes Injured by Hypoxia/Reoxygenation Wistar ventricular myocytes of neonatal rat aged 2 d are isolated under asepsis condition, then the myocytes are digested with mixture of digestive enzymes (0.06% trypsin and 0.1% type II collagenase mixed in equal amount) for multiple times in a short time. Cardiac myocytes are purified using differential adhesion method. The number of living cells and survival rate of cell are obtain by cell counting, and the cells are added in the plate of $1.0*10^6$ cell/ml medium. The cells are cultured for 24 hours, then the supernatant is discarded, and the cells are washed with PBS three times. All of the cells are classified into contrast group, hypoxia/reoxygenation injury group, hypoxia/reoxygenation model+compatible composition group 1 (30 μM), hypoxia/reoxygenation model+compatible composition group 3 (30 μM), hypoxia/reoxygenation model+compatible composition group 11 (30 μM), hypoxia/reoxygenation model+luteilon group (30 μM), hypoxia/reoxygenation model+kaempferol group (30 μM), and hypoxia/reoxygenation model+luteolin-7-O-glucoside group (30 μM). After pre-treatment for 24 h, all of the hypoxia/reoxygenation injury groups are placed in glucose-free Earle's solution which has been previously saturated with mixture of 95% $N_2$+5% $CO_2$ for 1 hour. The cells are cultured in hypoxic condition for 6 h at 37° C. in constant-temperature incubator introduced with the mixture of 95% $N_2$+5% $CO_2$. Then the hypoxia treated cells are subjected to reoxygenation in normal condition for 5 h with the DMEM high glucose medium (containing 10% FBS) which has been previously saturated with mixture of 95% air+5% $CO_2$. At the same time, the cells are incubated with the administration of compatible compositions. After treating the experimental groups of cells, 20 μg/ml MTT is added, and each experimental group is cultured for 4 h, then MTT is solved in 150 μl DMSO. OD of each well is read by ELISA meter at wavelength of 490 nm, and activity of cells is determined. The results are shown in table 4.

TABLE 4

Influence of the compatible composition on the activity of rat primary cardiac myocytes injured by nitrogen hypoxia/reoxygenation

| group number | dose (μM) | protection rate of (%) cell activity |
|---|---|---|
| control group | — | 97.75 ± 12.28 |
| model group | — | 59.95 ± 5.42### |
| compatible group 1 | 30 | 87.23 ± 8.56*** |
| compatible group 3 | 30 | 71.57 ± 7.53* |
| compatible group 11 | 30 | 62.15 ± 6.86 |
| Luteilon | 30 | 68.08 ± 6.38* |
| Kaempferol | 30 | 69.22 ± 6.22* |
| Luteolin-7-0-glucoside | 30 | 71.17 ± 7.72* |

Note:
Compared with the control group, ###$P < 0.001$,
compared with the model group, *$P < 0.05$,
***$P < 0.001$.

Analysis: compared with the blank control group, the cell activity of model group decrease significantly, indicating that rat primary cardiac myocytes model of hypoxia/reoxygenation injury has been establwashed successfully. Compared with the model group, compatible group 1, compatible group 3, compatible group 11 could protect cell activity on various levels, and the protective effect of compatible groups is better than individual compound.

V Influence of the Compatible Composition on LDH Leaking of Rat Primary Cardiac Myocytes Injured by Nitrogen Hypoxia/Reoxygenation Experiment Method: Wistar ventricular myocytes of neonatal rat aged 2 d are isolated under asepsis condition, then the myocytes are digested with mixture of digestive enzymes (0.06% trypsin and 0.1% type II collagenase mixed in equal amount) for multiple times in a short time. Cardiac myocytes are purified using differential adhesion method. The number of living cells and survival rate of cell are obtain by cell counting, and the cells are added in the plate of $1.0*10^6$ cell/ml medium. The cells are cultured for 24 hours, then the supernatant is discarded, and the cells are washed with PBS three times. All of the cells are classified into contrast group, hypoxia/reoxygenation injury group, hypoxia/reoxygenation model+compatible composition group. After pre-treatment for 24 h, all of the hypoxia/reoxygenation injury groups are placed in glucose-free Earle's solution which has been previously saturated with mixture of 95% $N_2$+5% $CO_2$ for 1 hour. The cells are cultured in hypoxic condition for 6 h at 37° C. in constant-temperature incubator introduced with mixture of 95% $N_2$+5%$00_2$. Then the hypoxia treated cells are subjected to reoxygenation in normal condition for 5 h with the high glucose medium DMEM (containing 10% FBS) which has been previously saturated with mixture of 95% air+5%OO$_2$. At the same time, the cells are incubated with compatible compositions. After treating the experimental groups of cells, the supernatant is collected; the content of LDH leak in supernatant of culture medium is measured according to the steps of LDH kit. The results are shown in table 5.

TABLE 5

Influence of the compatible composition on the LDH leak of rat primary cardiac myocytes injured by nitrogen hypoxia/reoxygenation

| group number | dose (μM) | Leak rate (%) of LDH |
|---|---|---|
| control group | — | 94.47 ± 5.60 |
| model group | — | 145.28 ± 14.80### |
| compatible group 1 | 30 | 88.53 ± 10.68*** |
| compatible group 3 | 30 | 94.32 ± 8.94*** |
| compatible group 11 | 30 | 98.62 ± 19.10*** |
| Luteilon | 30 | 122.37 ± 20.24* |
| Kaempferol | 30 | 111.25 ± 23.41* |
| Luteolin-7-0-glucoside | 30 | 115.18 16.05** |

Note:
Compared with the control group, ###p < 0.001;
compared with the model group, *P < 0.05,
P<0.01 and *P < 0.001.

Analysis: compared with the blank control group, the cell activity of the model group decrease significantly, indicating that rat primary cardiac myocytes model of hypoxia/reoxygenation injury has been established successfully. Compared with the model group, compatible group 1, compatible group 3, compatible group 11 can reduce leak of cell LDH on various levels, and the protective effects of compatible groups are better than individual compound.

VI Influence of the Compatible Composition on the pH of Supernatant of Rat Primary Cardiac Myocytes Injured by Nitrogen Hypoxia/Reoxygenation Experiment method: Wistar ventricular myocytes of neonatal rat aged 2 d are isolated under asepsis condition, then the myocytes are digested with mixture of digestive enzymes (0.06% trypsin and 0.1% type II collagenase mixed in equal amount) for multiple times in a short time. Cardiac myocytes are purified using differential adhesion method. The number of living cells and survival rate of cell are obtained by cell counting, and the cells are added in the plate of 1.0*10$^6$ cell/ml medium. The cells are cultured for 24 hours, then the supernatant is discarded, and the cells are washed with PBS three times. All of the cells are classified into contrast group, hypoxia/reoxygenation injury group, hypoxia/reoxygenation model+compatible composition group. After pre-treatment for 24 h, all of the hypoxia/reoxygenation injury groups are placed in glucose-free Earle's solution which has been previously saturated with mixture of 95% N$_2$+5% CO$_2$ for 1 hour. The cells are cultured in hypoxic condition for 6 h at 37° C. in constant-temperature incubator introduced with the mixture of 95% N$_2$+5% CO$^2$. Then the hypoxia treated cells are subjected to reoxygenation in normal condition for 5 h with the high glucose medium DMEM (containing 10% FBS) which has been previously saturated with mixture of 95% air+5% CO$_2$. At the same time, the cells are incubated with compatible compositions. After treating the experimental groups of cells, the supernatant is collected; the pH of supernatant of culture medium is measured directly with pH meter. The results are shown in table 6.

TABLE 6

Influence of the compatible composition on the LDH leak of rat primary cardiac myocytes injured by nitrogen hypoxia/reoxygenation

| group number | dose (μM) | pH of supernatant |
|---|---|---|
| control group | — | 7.19 ± 0.01 |
| model group | — | 6.87 ± 0.02## |
| compatible group 1 | 30 | 7.18 ± 0.01*** |
| compatible group 3 | 30 | 7.10 ± 0.01*** |
| compatible group 11 | 30 | 7.08 ± 0.02*** |
| Luteilon | 30 | 7.11 ± 0.01* |
| Kaempferol | 30 | 7.10 ± 0.01* |
| Luteolin-7-0-glucoside | 30 | 7.08 ± 0.02** |

Note:
Compared with the control group, ###p < 0.001;
compared with the model group, *P < 0.05,
P<0.01 and *P < 0.001.

Analysis: compared with the blank control group, the pH of supernatant of culture medium decrease significantly, indicating that hypoxia cardiac myocytes go through the process of sugar-free glycolysis, and lactic acid is largely produced, leading to the decrease of the pH of culture medium supernatant. Compared with the model group, compatible group 1, compatible group 3, compatible group 11 could reduce the pH of culture medium supernatant on various levels, indicating that the compositions could improve sugar-free glycolysis of cells and ameliorate metabolic disorder of cell energy. Besides, the protective effects of compatible groups are better than individual compound.

VII Influence of the Compatible Composition on ATP, ADP, and AMP of Rat Primary Cardiac Myocytes Injured by Nitrogen Hypoxia/Reoxygenation Experiment method: Wistar ventricular myocytes of neonatal rat aged 2 d are isolated under asepsis condition, then the myocytes are digested with mixture of digestive enzymes (0.06% trypsin and 0.1% type II collagenase mixed in equal amount) for multiple times in a short time. Cardiac myocytes are purified using differential adhesion method. The number of living cells and survival rate of cell are obtained by cell counting, and the cells are added in the plate of 1.0*10$^6$ cell/ml medium. The cells are cultured for 24 hours, then the supernatant is discarded, and the cells are washed with PBS three times. All of the cells are classified into contrast group, hypoxia/reoxygenation injury group, hypoxia/reoxygenation model+compatible composition group. After pre-treatment for 24 h, all of the hypoxia/reoxygenation injury groups are placed in glucose-free Earle's solution which has been previously saturated with mixture of 95% N$_2$+5% CO$_2$ for 1 hour. The cells are cultured in hypoxic condition for 6 h at 37° C. in constant-temperature incubator introduced with the mixture of 95% N$_2$+5% CO$_2$. Then the hypoxia treated cells are subjected to reoxygenation in normal condition for 5 h with the high glucose medium DMEM (containing 10% FBS) which has been previously saturated with mixture of 95% air+5% CO$_2$. At the same time, the cells are incubated with compatible compositions. After treating the experimental groups of cells, the culture solution is discarded. The cells are washed once with pre-cooled PBS. 500 μl pre-cooled 50% perchlorate solution is added in each well. Pyrolysis of cells take place on ice for 5 min. The cells are scrapped, 600 μl of 2.5 mol/L Na$_2$CO$_3$ solution is added, and pH is adjusted to 6.5. Pyrolysis mixture is collected in centrifuge tube and centrifuged in 4° C. Content of supernatant is determined by HPLC.

0.5 mg of ATP, ADP, and AMP are accurately weighed respectively, solved with phosphate buffer, and diluted to concentration gradients of 0.625, 1.25, 2.5, 5, 10, 20, 40 μg/ml.

The content is determined with HPLC method. The equipment is LC-2010C quaternionic pump high performance liquid chromatogram, analytical column is Diamonsil C18 column (250 mm×4.6 mm, 5 μm), detection wavelength: 260 nm, mobile phase is 0.05M phosphate buffer (pH 6.5), detector is UV-vis detector. Flow-rate of column is 0.8 ml/min, sample size is 20 μl, and analytical time is 12 min, the data is processed using LCsolution chromatography workstation (Japan, SHIMATSU). The results are shown in table 7.

TABLE 7

Influence of the compatible composition on the high-energy phosphate of rat primary cardiac myocytes injured by nitrogen hypoxia/reoxygenation

| group number | dose (μM) | ATP(μg/mL) | ADP(μg/mL) | AMP(μg/mL) |
| --- | --- | --- | --- | --- |
| control group | — | 136.45 ± 2.92 | 3.99 ± 0.23 | 3.02 ± 0.21 |
| model group | — | 65.32 ± 6.96# | 39.26 ± 1.13## | 38.06 ± 4.49## |
| compatible group 1 | 30 | 120.65 ± 7.94*** | 13.43 ± 2.01*** | 5.48 ± 0.32*** |
| compatible group 3 | 30 | 96.95 ± 3.21** | 17.54 ± 1.85** | 8.21 ± 0.45** |
| compatible group 11 | 30 | 73.52 ± 4.65* | 19.58 ± 1.47* | 9.31 ± 0.12* |
| Luteilon | 30 | 102.88 ± 4.98* | 15.38 ± 1.35** | 7.59 ± 0.08** |
| Kaempferol | 30 | 84.72 ± 1.06* | 17.15 ± 1.84** | 7.15 ± 0.87** |
| Luteolin-7-0-glucoside | 30 | 69.45 ± 1.11 | 17.12 ± 1.47** | 8.97 ± 0.63* |

Note:
Compared with the control group, ###$p < 0.001$;
compared with the model group, *$P < 0.05$,
$P<0.01$ and *$P < 0.001$.

Analysis: compared with the blank control group, the ATP content decrease significantly, the content of ADP, AMP increased significantly. Compared with the model group, compatible group 1, compatible group 3, compatible group 11 could increase ATP content and reduce ADP, AMP content on various levels, indicating that the compositions could ameliorate metabolic disorder of cells energy. Besides, the protective effects of compatible groups are better than individual compound.

DESCRIPTION OF THE PREFERRED EMBODIMENTS

First Embodiment

Example 1

Figure 1:
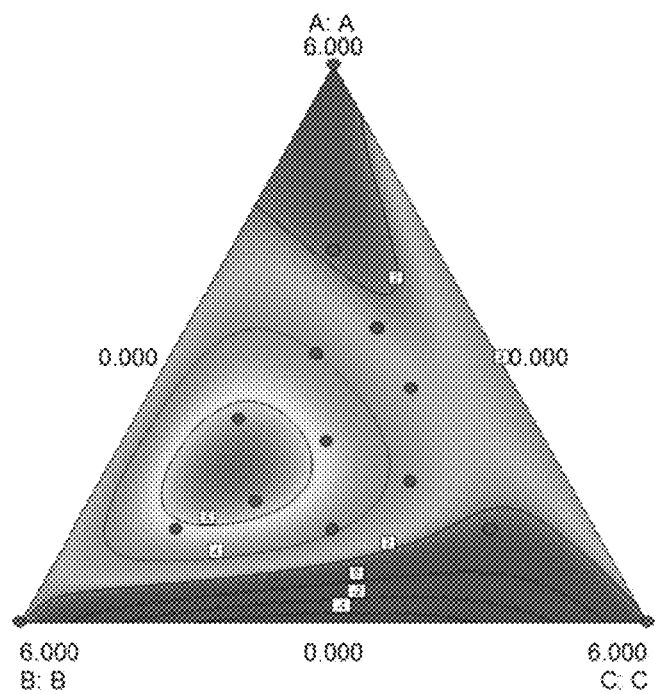
FIG. 1 is the 3D kyrtograph and contour map by fitting analyze the protective effect of compatible group comprising luteilon, kaempferol and luteolin-7-O-glucoside on cells energy of hypoxia/reoxygenation injured H9C2 cells.
Figure 1:
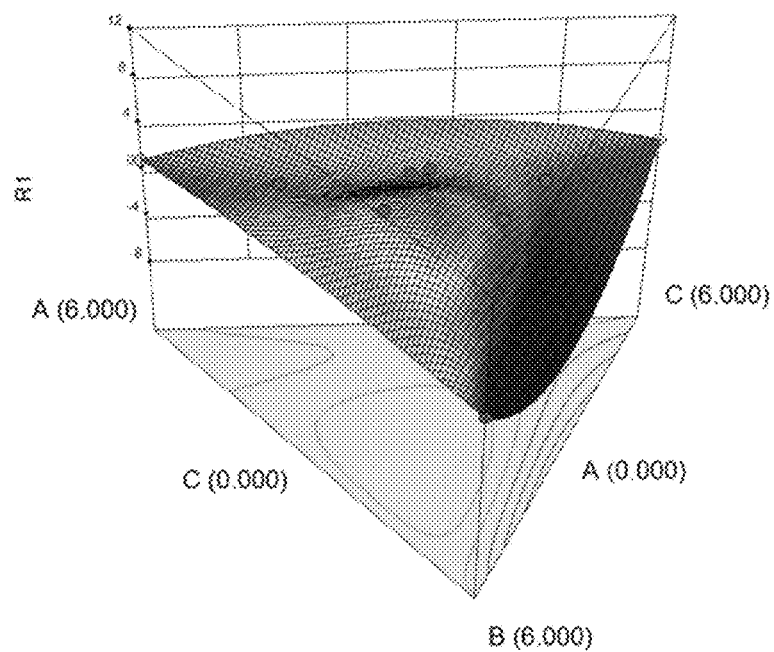
Figure 2:
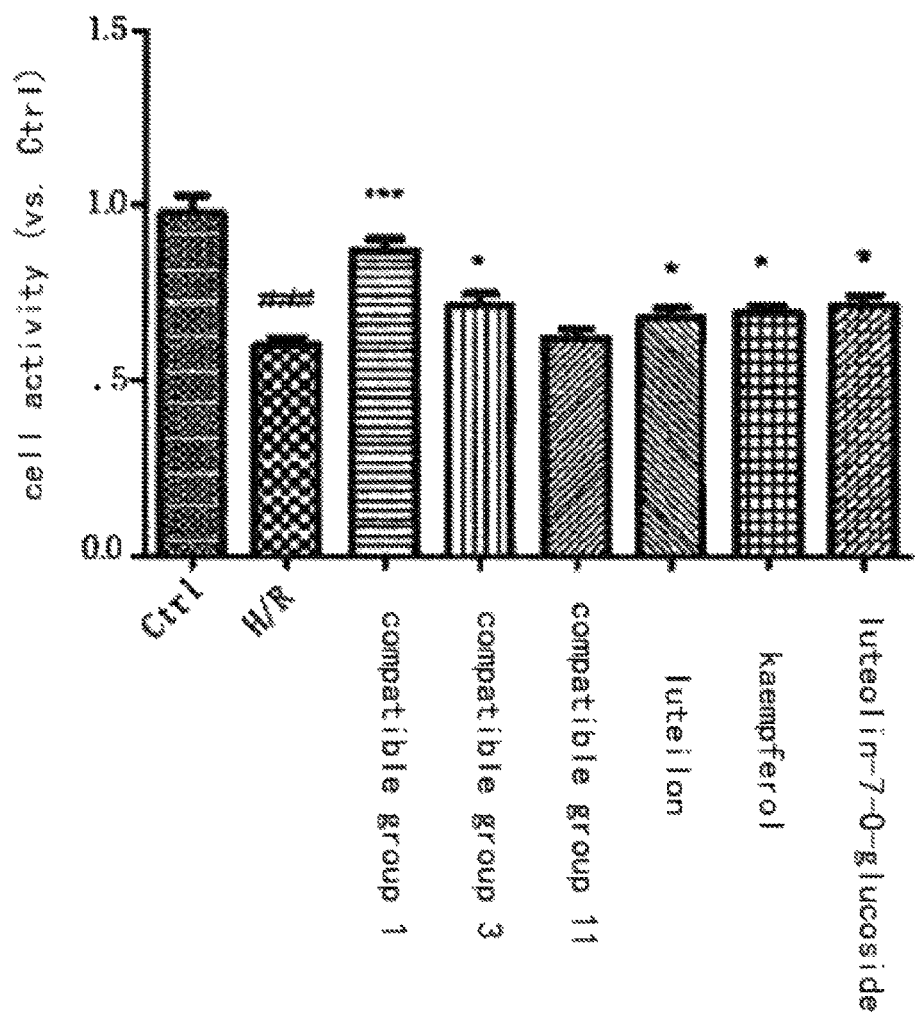
FIG. 2 shows the variation of cells energy of rat primary cardiac myocytes after hypoxia/reoxygenation injury.

| Tablet (content per tablet) | |
| --- | --- |
| luteilon | 44.5 mg |
| kaempferol | 111.7 mg |
| luteolin-7-O-glucoside | 173.8 mg |
| lactose | 90.0 mg |
| starch | 38.0 mg |
| carboxymethyl starch sodium | 20.0 mg |
| avicel | 20.0 mg |
| dolomol | 2.0 mg |
| total | 500 mg |

The powder of each component in table above is mixed, compressed by the tablet machine, to make the tablet of 500 mg. the tablets can be film-coated or sugar-coated as needed.

Second Embodiment

Example 2

| Tablet (content per tablet) | |
| --- | --- |
| luteilon | 50.3 mg |
| kaempferol | 201.0 mg |
| luteolin-7-O-glucoside | 78.7 mg |
| lactose | 90.0 mg |
| starch | 38.0 mg |
| carboxymethyl starch sodium | 20.0 mg |
| avicel | 20.0 mg |
| dolomol | 2.0 mg |
| total | 500 mg |

The powder of each component in table above is mixed, compressed by the tablet machine, to make the tablet of 500 mg. the tablets can be film-coated or sugar-coated as needed.

What is claimed is:

1. A method for treating myocardial ischemia-reperfusion injury comprising administering a pharmaceutical composition comprising luteolin, kaempferol, luteolin-7-O-glucoside and a pharmaceutically accepted carrier, wherein the molar ratio among luteolin, kaempferol and luteolin-7-O-glucoside is 0.7-2.2:2.1-4.1:0.6-2.4.

2. The method according to claim 1, wherein the molar ratio among luteolin, kaempferol and luteolin-7-O-glucoside is 1.1-1.6:2.8-3.5:1.0-1.7.

3. The method according to claim 1, the pharmaceutical composition being selected from the group consisting of a tablet, granule, capsule, injection and aerosol.

4. A method for treating myocardial ischemia-reperfusion injury comprising administering a pharmaceutical composition consisting of pharmaceutical active component and pharmaceutically accepted carrier, the pharmaceutical active components comprising luteolin, kaempferol, luteolin-7-O-glucoside, wherein the molar ratio among luteolin, kaempferol and luteolin-7-O-glucoside is 1.1-1.6:2.8-3.5:1.0-1.7.

* * * * *